United States Patent [19]
Seitz

[11] Patent Number: 5,435,320
[45] Date of Patent: Jul. 25, 1995

[54] METHOD AND APPARATUS FOR SENSING AND EVALUATING BALANCE

[76] Inventor: Ronald H. Seitz, 3202 E. Race St., Visalia, Calif. 93291

[21] Appl. No.: 10,840

[22] Filed: Jan. 29, 1993

[51] Int. Cl.⁶ .............................................. A61B 5/103
[52] U.S. Cl. .................................................... 128/782
[58] Field of Search ................. 128/774, 779, 782; 273/449; 73/65

[56] References Cited

U.S. PATENT DOCUMENTS

| | | |
|---|---|---|
| 2,253,996 | 8/1941 | Bechman . |
| 3,352,559 | 11/1967 | Larsen . |
| 3,712,294 | 1/1973 | Muller .................. 128/782 |
| 3,826,145 | 7/1974 | McFarland ............. 128/782 |
| 3,906,931 | 9/1975 | Terekhov ............... 128/782 |
| 4,099,713 | 7/1978 | Spector . |
| 4,320,895 | 3/1982 | Muller . |
| 4,463,946 | 8/1984 | Wallace et al. . |
| 4,759,542 | 7/1988 | Hudec . |
| 4,944,309 | 7/1990 | Mechling . |

*Primary Examiner*—Max Hindenburg
*Attorney, Agent, or Firm*—Worrel & Worrel

[57] ABSTRACT

A method for sensing balance in a person including the steps of: positioning the person on an unstable surface of support; having the person perform a preinstructed task; and detecting the person's performance of the task. An apparatus for sensing balance in a person, the apparatus including a platform dimensioned to receive a person in supported relation thereon; and a member for supporting the platform for movement along a course under the impetuous of a person supported on the platform whereby the balance of the person can be sensed.

11 Claims, 2 Drawing Sheets

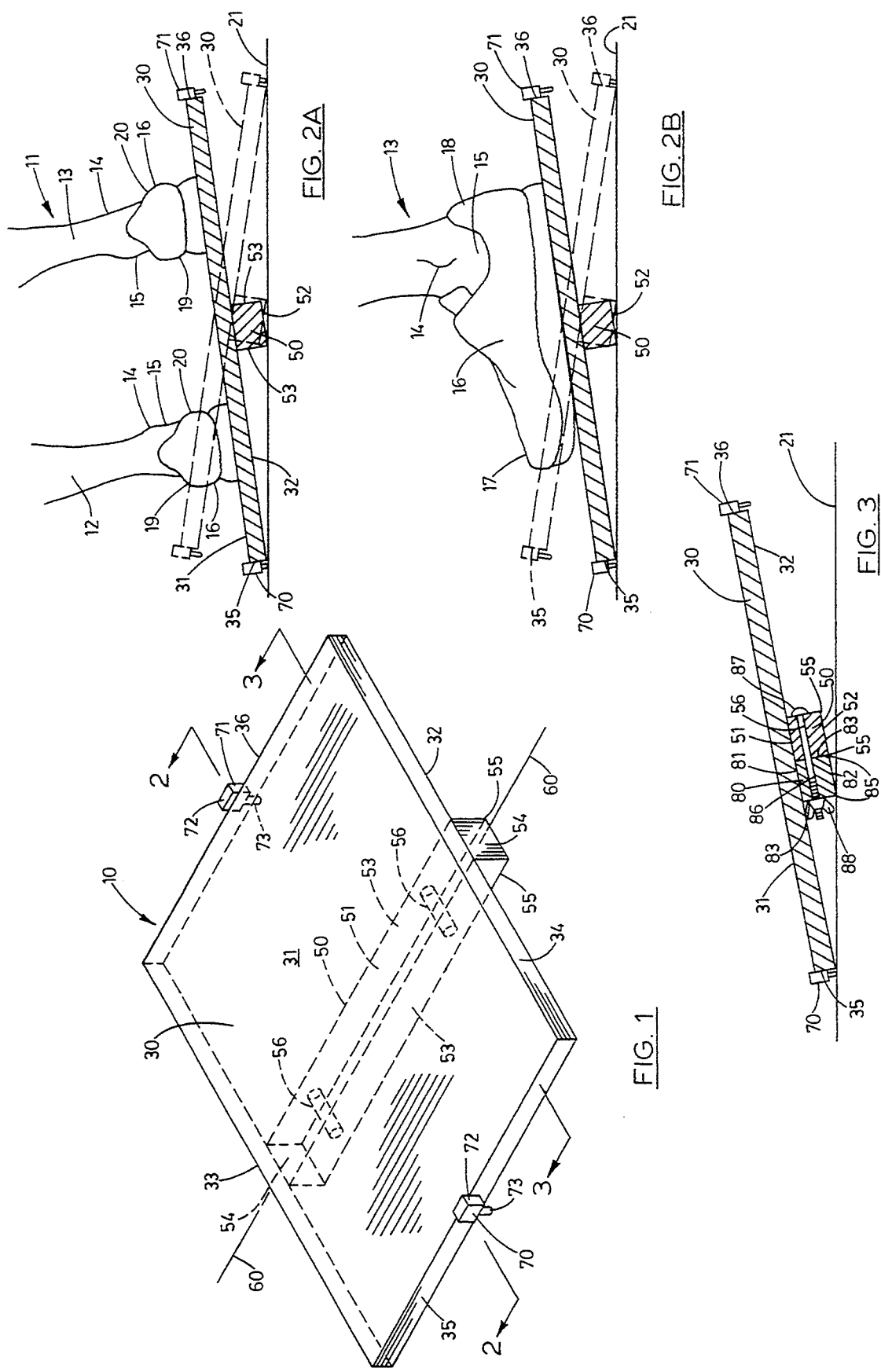

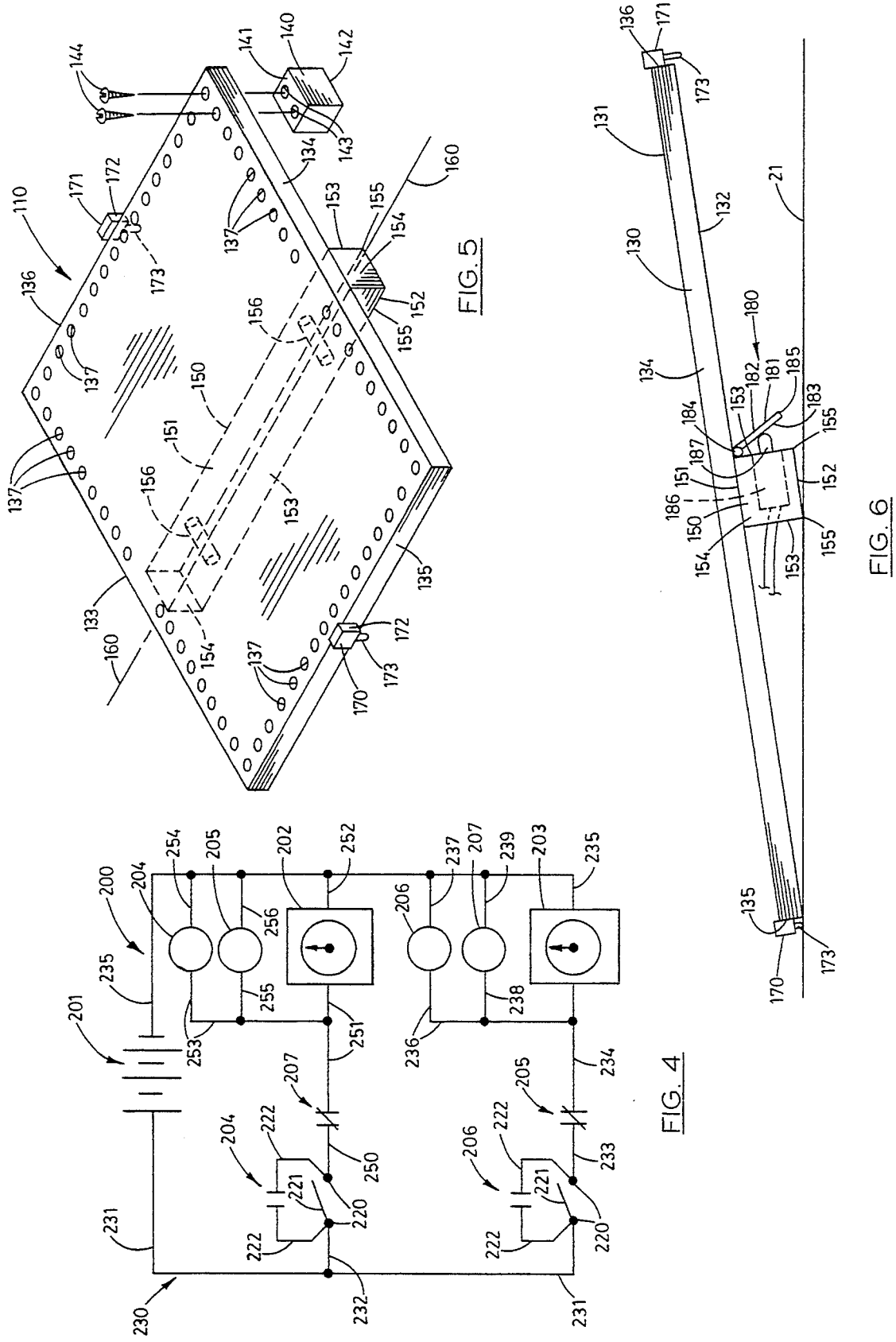

METHOD AND APPARATUS FOR SENSING AND EVALUATING BALANCE

BACKGROUND OF THE INVENTION

1. Field of the Invention

The present invention relates to a method and apparatus for sensing and evaluating balance and, more particularly, to such a method and apparatus which are particularly useful in isolating for evaluation the physical capabilities of persons having an impaired sense of balance.

2. Description of the Prior Art

The sense of balance in human beings is critical to a wide variety of physical activities. It has long been known that this sense of balance is dependent upon a number of physical capabilities and environmental circumstances. Thus, it is known that such physical capabilities as sensing by the vestibular system of the inner ear, the somatosensory system, vision, strength, range of motion and the capability for flexion and extension of portions of the body influence the capability for maintaining balance. As to the environmental circumstances, such conditions as the stability of the supporting surface, time, control and general physical environment can influence the capability for maintaining balance.

More recently, it has become known that other, more subtle influences also affect the ability to maintain balance. For example, there are cognitive and noncognitive abilities which play a part in a person's capability for maintaining balance. Thus, noncognitive responses to physical stimuli influence the ability to maintain balance. Physiotherapists, for example, refer to capabilities of this type as "engrams." Engrams refer to the body's instinctive ability to react to even very subtle physical stimuli to maintain balance, such as by extension or flexion of the legs to shift the body's center of gravity. The speed and rapidity with which the human body can so respond, plays a considerable part in the overall balance capability of the individual.

Knowledge of the multitude of individual factors so influencing the overall balance capability is of particular importance in developing programs of rehabilitation for persons with physical disabilities due to such causes as disease, injury, age and the like. There has not heretofore been a means by which these factors could successfully be isolated for evaluation in the process of developing a plan for rehabilitation of such individuals.

Therefore, it has long been known that it would be desirable to have a method and apparatus for sensing and evaluating balance which is capable of use in isolating one or more of the factors influencing a person's capability of maintaining balance; which can be employed as a diagnostic tool in evaluating a person's sense of balance for purposes of designing a program of rehabilitation specifically suited to that individual; which can be employed by the individual in practicing the capabilities required in maintaining balance so as to develop new skills relative thereto; which can be constructed in a wide variety of forms specifically directed to the particular diagnostic requirements; and which is inexpensive to acquire and use.

SUMMARY OF THE INVENTION

Therefore, it is an object of the present invention to provide an improved method and apparatus for sensing and evaluating balance.

Another object is to provide such a method and apparatus which are particularly well suited to use in the treatment of persons requiring rehabilitation due to incapacities resulting from disease, injury, age and the like.

Another object is to provide such a method and apparatus which are uniquely well suited to use as a diagnostic tool in the rehabilitation of persons suffering from a broad range of incapacities.

Another object is to provide such a method and apparatus which possess the capability for isolating one or more factors having a direct influence on a person's capability for maintaining balance and for purposes of developing a program of rehabilitation specifically directed to the incapacities of the individual under consideration.

Another object is to provide such a method and apparatus which can be used by the individual in accordance with a rehabilitation program allowing the individual to develop the senses and physical capabilities required for improved performance.

Another object is to provide such a method and apparatus which are inexpensive to employ, have a wide scope of application and which can be reconfigured to meet the specific requirements of the individual.

Another object is to provide such a method and apparatus which are operable to convert subjective cognitive and noncognitive abilities into objective data suitable for reliable evaluation.

Further objects and advantages are to provide improved elements and arrangements thereof in an apparatus for the purpose described which is dependable, economical, durable and fully effective in accomplishing its intended purpose.

These and other objects and advantages of the present invention are achieved, in the preferred embodiment of the present invention in a method for sensing balance in a person including the steps of positioning the person on an unstable surface of support; having the person perform a preinstructed task; and detecting the person's performance of the task and in an apparatus for the purpose described including a platform dimensioned to receive a person in supported relation thereon; and a member for supporting the platform for movement along a course under the impetus of a person supported on the platform whereby the balance of the person can be sensed.

BRIEF DESCRIPTION OF THE DRAWINGS

FIG. 1 is a perspective view of the first embodiment of the sensing apparatus of the present invention.

FIG. 2A is a transverse vertical section taken from a position indicated by line 2—2 in FIG. 1, showing the feet and legs of a test subject supported thereon for illustrative convenience in a first attitude and showing the sensing apparatus in full lines in a first operative position and in phantom lines in a second operative position.

FIG. 2B is a transverse vertical section taken from a position indicated by line 2—2 in FIG. 1, showing the legs and feet of a test subject supported thereon for illustrative convenience in a second attitude and showing the sensing apparatus in full lines in a first operative position and in phantom lines in a second operative position.

FIG. 3 is a transverse vertical section taken from a position indicated by line 3—3 in FIG. 1 and showing a lateral extension in an installed position.

FIG. 4 is a schematic diagram of an electrical system for the first and second embodiments of the sensing apparatus of the present invention.

FIG. 5 is a perspective view of the second embodiment of the sensing apparatus of the present invention.

FIG. 6 is a somewhat enlarged, side elevation of the sensing apparatus of the second embodiment of the present invention shown for illustrative convenience on a supporting surface and mounting a lateral extension assembly.

DESCRIPTION OF THE PREFERRED EMBODIMENTS

First Embodiment

The sensing apparatus of the first embodiment of the present invention operable in the practice of the method of the present invention is generally indicated by the numeral 10 and is shown in FIGS. 1, 2A, 2B, 3 and 4. As shown in FIGS. 2A and 2B, a test subject, or person, is supported on tile sensing apparatus and is generally indicated by the numeral 11. For illustrative convenience it will be understood that the test subject has a left leg 12, a right leg 13, ankles 14 and feet 15. A shoe 16 is worn on each foot of tile test subject. The foot and shoe of the person can be viewed as having a front 17, a rear 18, a left side 19, and a right side 20. As shown in FIGS. 2A, 2B and 3, the sensing apparatus 10 is rested on a planar, or supporting surface 21.

The sensing apparatus 10 has a rectangular, flat platform 30 having an upper surface 31, a parallel lower surface 32, a front surface 33 and a parallel rear surface 34. The platform has a left side surface 35 and an opposite, parallel right side surface 36. The platform can be constructed of any suitable material including wood, metal, high strength plastic, or the like.

A pivot member 50 is mounted on the lower surface 32 of the platform 30 extending frown the front surface 33 to the rear surface 34. A pivot member has a flat upper surface 51, mounted as, for example, by adhesive, on the lower surface 32 of the platform. The pivot member has a lower surface 52 parallel to the upper surface 51 and to the lower surface 32 of the platform. The pivot member has parallel opposite side surfaces 53 and similarly parallel end surfaces 54. The pivot member is rectangular in cross section having parallel lower edges 55. A pivot member can be constructed of any suitable hard material such as wood, metal, high strength plastic or the like. A pair of transverse bolt holes 56 extend through the pivot member and the side surfaces 53 thereof in spaced, parallel relation to each other. The pivot member is oriented along a longitudinal axis 60 which, in the preferred embodiment, is precisely midway between the left side surface 35 of the platform and the right side surface 36 thereof. A longitudinal axis is parallel to the left and right side surfaces.

A micro switch 70 is mounted on the left side surface 35 of the platform 30. A micro switch 71 is mounted on the right side surface 36 of the platform. Each of the micro switches has a housing 72 from which is extended a plunger 73 which, in the fully extended attitude, extends beneath the lower surface 32 of the platform. The micro switches are each of the normally opened form, as will hereinafter be discussed in greater detail, wherein the switches are open when the plunger 73 is in the fully extended attitude and closed when the plunger is depressed from the fully extended attitude.

Referring more particularly to FIG. 3, the sensing apparatus 10 is adapted to receive a lateral extension 80.

The lateral extension is of substantially the same length, width and depth as the pivot member 50 and is, similarly, rectangular in cross section. The lateral extension has a flat upper surface 81, an opposite, flat lower surface 82 parallel to the upper surface, and parallel, flat side surfaces 83. The lateral extension has parallel lower edges 85, transverse bolt holes 86 extending therethrough in positions corresponding to the transverse bolt holes 56 of the pivot member. The lateral extension 80 is adapted to be mounted, if desired, in side-by-side relation to the pivot member as shown in FIG. 3. In this configuration, the pivot member and lateral extension are disposed in side-by-side relation with the right side surface 83 in facing engagement with the left side surface 53 of the pivot member. Bolts 87 are individually extended through the transverse bolt holes 56 and 86 of the pivot member and lateral extension, respectively. Wing nuts 88 are individually screw-threadably secured on the bolts to mount the lateral extension 80 securely in the position described. As will hereinafter be described in greater detail, the lateral extension can be installed or removed in accordance with the desire of the person operating the sensing apparatus, such as a physiotherapist.

Second Embodiment

The sensing apparatus of the second embodiment of the present invention is generally indicated by the numeral 110 and is shown in FIGS. 5 and 6. The sensing apparatus has a rectangular, flat platform 130 which, except as hereinafter noted, is identical to the platform 30 of the first embodiment of the invention. The platform 130 has a flat upper surface 131 and an opposite parallel flat lower surface 132. The platform has a flat front surface 133 and an opposite flat, parallel rear surface 134. The platform has a flat left side surface 135 and an opposite, flat right side surface 136 which is parallel to the left side surface. A plurality of screw holes 137 are individually extended through the platform adjacent to the periphery thereof, preferably with uniform spacing, so as to extend through the upper and lower surfaces 131 and 132 in right angular relation thereto. The screw holes are arranged in pairs of equal spacing.

An auxiliary block 140 is adapted to be mounted on the platform 130. The auxiliary block can be constructed of wood, metal, high strength plastic or the like. The auxiliary block is preferably a cube having a flat upper surface 141 and an opposite, flat, parallel lower surface 142. A pair of internally screw threaded screw holes 143 extend into the upper surface 141 of the block in a pattern corresponding to the pattern of each pair of screw holes 137 of the platform. The auxiliary block is adapted selectively to be mounted on the lower surface 132 of the platform 130 by positioning the upper surface 141 of the auxiliary block in facing engagement with the lower surface 132 of the platform and with the screw holes 143 thereof in alignment with a pair of the screw holes 137 of the platform. Screws 144 individually extended through the screw holes 137 of the pair and screw-threadably secured in the screw holes 143 of the auxiliary block 140 to mount the block in the position desired. It will be seen that the auxiliary block can thus be mounted in a plurality of positions extending about the periphery of the platform in alignment with each pair of screw holes. The purpose therefore in the practice of the method of the present invention will hereinafter be described in greater detail.

The sensing apparatus 110 has a pivot member 150 substantially identical to that of the pivot member 50 of the sensing apparatus 10 of the first embodiment of the present invention. The pivot member has a flat tipper surface 151, an opposite, flat parallel lower surface 152 and flat parallel side surfaces 153. A pivot member 150 has parallel end surfaces 154 individually in the same planes with the respective front surface 133 and rear surface 134. The pivot member has parallel lower edges 155 and a pair of transverse bolt holes 156 extending therethrough. The pivot member can be constructed of any suitable material, such as wood, metal, high strength plastic or the like. The pivot member 150 has a longitudinal axis 160 and is mounted on the lower surface 132 of the platform, such as by adhesive, with the upper surface 151 thereof in facing engagement with the lower surface 132 of the platform. When so mounted in position, the longitudinal axis 160 of the pivot member is precisely midway between the left side surface 135 of the platform and the right side surface 136 thereof and is parallel thereto.

As in the case of the sensing apparatus 10 of the first embodiment of the invention, a micro switch 170 is mounted on the left side surface 135 of the platform 130 of the sensing apparatus 110. A micro switch 17 1 is mounted on the right side surface 136 of the platform. Each of the micro switches has a housing 172 from which a plunger 173 is extended. Each micro switch is mounted so that the plunger 173 when in the fully extended attitude extends beneath the lower surface 132 of the platform 130 as shown in FIG. 6. As with the micro switches of the sensing apparatus 10, the micro switches 170 and 171 are normally open switches which close when the plunger 173 thereof is moved from the normal, fully extended attitude.

The sensing apparatus 110 is adapted to receive a lateral extension such as lateral extension 80 of the sensing apparatus 10 previously described. Referring more particularly to FIG. 6, however, the sensing apparatus 110 is shown in FIG. 6 mounting a different lateral extension assembly 180. The lateral extension assembly 180 has a metal pivot plate 181 having an outer surface 182 and an inner surface 183 pivotally mounted on a pivot, or hinge, assembly 184 mounted on the lower surface 132 of the platform 130. The pivot plate has a straight distal edge 185 and is operable to be pivoted about the hinge assembly 184 by an electrical solenoid 186 mounted on the lower surface 132 of the platform. The electrical solenoid has a plunger 187 mounted on the inner surface 183 of the pivot plate. The electrical solenoid is operable through an electrical system, not shown, of any suitable type to move the pivot plate to any selected position about the hinge assembly 184 and between the electrical solenoid and the lower surface 132 of the platform.

Referring more particularly to FIG. 4, an electrical system 200 for the sensing apparatus 10 of the first embodiment of the present invention and for the sensing apparatus 110 of the second embodiment of the present invention is shown in the schematic diagram thereof. As shown in FIG. 4, the electrical system has a source of electrical energy 201, a first clock, or timer, 202 and a second clock, or timer 203. The timers can be of any suitable type individually operable upon electrical energy being supplied thereto to record time until the flow of electrical energy thereto is terminated. Upon such tinting and a termination of the flow electrical energy thereto, each timer operates to continue to register the time recorded. Preferably the timers are operable individually to time, record and continually individually to display a plurality of individual times. The individual times are thus available for the physiotherapist to record for purposes of subsequent evaluation.

The electrical system 200 has a first control relay 204, which is normally open, and a second control relay 205 which is normally closed. The electrical system has a third control relay 206, which is normally open, and a fourth control relay 207 which is normally closed. The first and third control relays have a pair of electrical contacts 220 capable of being bridged by a normally open switch 221. The first and third control relays each include a pair of electrical conductors 222 terminating in electrical contacts.

It will be understood that in the case of the sensing apparatus 10, the plunger 73 of the micro switch 70 is operably connected to the normally open switch 221 of the first control relay 204. In the case of the sensing apparatus 110, the plunger 173 of the micro switch 170 is operably connected to the normally open switch 221 of the first control relay 204. Similarly, in the case of the sensing apparatus 10, the plunger 73 of the micro switch 71 is operably connected to the normally open switch 221 of the third control relay 206. In the case of sensing apparatus 110, the plunger 173 of micro switch 171 is operably connected to the normally open switch 221 of the third control relay 206. In the conventional manner, when either plunger closes its respective switch 221, the first or third control relay thereof maintains the normally open switch 221 in the closed condition for purposes hereinafter described.

Electrical system 200 has an electrical circuit 230 interconnecting the operative components thereof and hereinafter described. The electrical circuit includes an electrical conductor 231 operably interconnecting the source of electrical energy 201 and the electrical contact 220 of the third control relay 206. Electrical conductor 232 operably interconnects electrical 23 1 and electrical contact 220 of the first control relay 204. Electrical conductor 233 operably interconnects electrical contact 220 of the third control relay 206 and the normally closed second control relay 205. Electrical conductor 234 operably interconnects the second control relay 205 and the second timer 203. Electrical conductor 235 interconnects the second timer 203 and the source of electrical energy 201. Electrical conductor 236 operably interconnects electrical conductor 234 and the third control relay 206. Electrical conductor 237 operably interconnects the third control relay and electrical conductor 235. Electrical conductor 238 operably interconnects electrical conductor 236 and the fourth control relay 207. Electrical conductor 239 operably interconnects the fourth control relay 207 and electrical conductor 235.

Electrical conductor 250 operably interconnects electrical contact 220 of the first control relay 204 and the normally closed fourth control relay 207. Electrical conductor 25 1 operably interconnects the fourth control relay and the first timer 202. Electrical conductor 252 operably interconnects the first timer 202 and electrical conductor 235. Electrical conductor 253 operably interconnects electrical conductor 251 and the first control relay 204. Electrical conductor 254 operably interconnects the first control relay 204 and electrical conductor 235. Electrical conductor 255 operably interconnects electrical conductor 253 and the second control relay 205. Electrical conductor 256 operably interconnects the second control relay 205 and electrical conductor 235.

OPERATION

The operation of the described embodiments of the subject invention in the practice of method of the present invention is hereinafter described. In doing so, the operation of the sensing apparatuses 10 and 110 can conveniently be described simultaneously, except as otherwise specifically set forth. In the following description, it will be understood that the test subject 11 is the person having a physical disability of one form or another. The person practicing the method of the present invention and operating the apparatuses in furtherance of this objective can be a doctor, physiotherapist or the like. For purposes of illustrative convenience, this person will hereinafter be referred to as a physiotherapist with the understanding that he is simply representative of any such person performing this function.

The specific operation of the sensing apparatuses 10 and 110 and the variants thereof shown in FIGS. 3 and 6, as well as the various embodiments which the method of the present invention can take, are dependent to a significant extent upon the specific purpose for using the sensing apparatus. This specific purpose is dependent upon the condition of the test subject 11 and the objective information to be gathered. For example, if the test subject, due to disease, age, injury or the like, requires rehabilitation, an initial evaluation of the physical incapacities of the test subject should be performed. Since a sense of balance is critical to the successful performance of wide variety of physical activities, the test subject may be seeking rehabilitation relative to one or more physical deficiencies. However, if the test subject notices a disability relative to one 2physical activity, the probability is that the deficiencies exist, to one degree or another, relative to a wide range of physical activities. Accordingly, rather than seeking to rehabilitate one physical activity, the physiotherapist should seek to treat the cause, or causes, of the physical disability rather than simply one or a few manifestations thereof. The initial evaluation is directed to this purpose.

Once this initial evaluation has been completed and the particular configuration of the sensing apparatuses 10 or 110 determined, the practice of the method of the present invention can continue. A first type of test which can be conducted in accordance with the method and apparatus of the present invention may best be visualized upon reference to FIG. 2A. The test subject 11 typically is directed to stand on the upper surface 31 of the platform 30 facing the front surface 33 thereof with the test subject's shoes 16 disposed equal distances on opposite sides of the pivot member 50 and substantially parallel thereto. In one application of the method of the present invention, the test subject is directed to maintain the platform 30 in a precisely horizontal attitude for a stated period of time, or for as long as the test subject is capable of doing so. More specifically, the test subject maintains the lower surface 52 of the pivot member 50 in facing engagement with the supporting surface 21. During the test, the physiotherapist conducting the test obtains objective information in the form of the time recorded during the test. However, the person conducting the test also obtains subjective information in noting the ease with which the test subject maintains balance, is able to achieve this objective by extension and flexion of the legs and the like. Both types of data are useful in evaluating the capabilities of the test subject.

A second type of test of the method of the present invention is depicted in FIG. 2A. During this test, the test subject 11 is directed to stand on the upper surface 31 of the platform 30 in the relationship previously described and as shown in FIG. 2A. The test subject is then directed to move the platform from the position shown in full lines in FIG. 2A to the position shown in phantom lines in FIG. 2A and then to return the platform again to the position shown in full lines in FIG. 2A. In addition, typically in accordance with the method of the present invention, the test subject is directed to repeat this process a given number of times or cycles. Thus, for example, the test subject may be directed to repeat this process ten times. In addition, and again depending upon the decisions made by the physiotherapist in the initial evaluation, the test subject may be directed to perform this process in such manner as to attempt to have the time required for the platform to move from the position shown in full lines in FIG. 2A to the position shown in phantom lines in FIG. 2A to be as precisely identical to the time required to move the platform from the position shown in phantom lines in FIG. 2A to the position shown in full lines therein.

In this regard, referring more particularly to FIG. 4, when the test subject 11 moves the platform 30 from the horizontal start position to the position shown in full lines in FIG. 2A, the plungers 73 and 173 of the micro switches 70 and 170 are depressed so as to move from the fully extended attitudes and thereby to close the switches 221 of those micro switches.

The operation of the electrical system 200 will now be described as it operates in both of the sensing apparatuses 10 and 110. As previously described, the closure of switch 221 causes the first control relay 204 to maintain the normally open switch 221 in the closed position. Accordingly, electrical energy is supplied from the source of electrical energy 201 to start and continue operation of the first timer 202. The first timer continues to run to record the time as the test subject moves the platforms 30 and 130 along the course from the position shown in full lines in FIG. 2A to the position shown in phantom lines therein. As previously discussed, when the plungers 73 and 173 of the micro switches 71 and 171 comes into engagement with the supporting surface 21, the plunger is depressed thereby closing the normally open switch 221 of that micro switch. Upon closure of the switch 221 of that micro switch, the third control relay 206 is energized to maintain the normally open switch 221 in the closed position. This allows electrical energy to flow from the source of electrical energy 201 to the second timer 203 thereby starting and continuing operation of the second timer 203 to record time. Simultaneously, electrical energy is supplied to the fourth control relay 207 which causes it to open and thereby terminate the flow of electrical energy to the first timer 202. In addition, opening of normally closed fourth control relay 207 terminates the flow of electrical energy to the first control relay 204 thereby allowing switch 221 of micro switches 70 and 170 to open. As the test subject moves the platform from the position shown in phantom lines in FIG. 2A to the position shown in full lines in FIG. 2A, the second timer 203 continues to record the time required for the test subject to do so.

Upon the plungers 73 and 173 of the micro switches 70 and 170 being depressed by contact with the supporting surface 21, the switch 221 of the micro switches 70 and 170 is again closed as previously described thereby starting and continuing operation of the first timer 202 to record time. Simultaneously with this occurrence, electrical energy is supplied to the second control relay 205 causing it to open and thereby terminate the flow of electrical energy to the second timer 203. At the same time, electrical energy is no longer supplied to the third control relay 206 which permits the switch 221 of the micro switches 71 and 171 again to return to the normally open position.

The test subject repeats the cycles of performance moving the platform back and forth between the position shown in full lines in FIG. 2A and the position shown in phantom lines therein. Since the first and second timers 202 and 203 are capable of recording multiple independent times, a complete record of the times required in each direction along the course is recorded and is available for the physiotherapist for purposes of evaluating the physical capability of the test subject.

A third test conducted in accordance with the method of the present invention is depicted in FIG. 2B. In this test, the test subject 11 stands on the platforms 30 and 130 in the position relative to the pivot members 50 and 150 depicted in 2B. Typically, the feet 15 and shoes 16 of the test subject are spaced from each other a comfortable distance, or in other words, approximately as shown in FIG. 2A. Thereafter, the physiotherapist directs the test subject to perform the cycles of operation described in relation to the second test depicted in FIG. 2A. Since the functioning of the sensing apparatuses 10 and 110 in this test is otherwise identical to that described in relation to the second test, it need not be repeated here.

In some instances, the physiotherapist may want the test subject to have, in effect, a more complex course to follow in repeating the cycles previously described in relation to the second and third test. As shown in FIG. 3, this may be achieved by mounting the lateral extension 80 on the apparatus as previously described. This can be done without the test subject being advised, if desired. The consequence of this is that the parallel lower edges 55 of the pivot member 50 are, in effect, moved to twice the distance apart in that the course is defined in part by contact of the left parallel edge 85 of the lateral extension and the right parallel edge 55 of the pivot member defining axes about which the platform must rock in following the course previously described. This adds an additional circumstance with which the test subject must deal. In addition, the enlarged flat surface area of the pivot member and lateral extension encountered by the test subject in mid course requires greater extension and flexion of the legs 12 and 13 in overcoming the effect of gravity. This effect, of course, applies to all of the tests heretofore described.

Another method for achieving a similar result is depicted in FIG. 6. The effective parallel edges of the pivot member 150, as shown therein, are parallel edge 155 and distal edge 185. The electrical solenoid 186 is operated to select the precise width for the pivot member desired in a performance of the test heretofore described. Thus, the electrical solenoid can be operated to move the distal edge 185 to a position disposed in immediate side-by-side relation to parallel lower edge 155 on the right as viewed in FIG. 6. Alternatively, the electrical solenoid can be operated to pivot the pivot plate 181, for example, to the position shown in FIG. 6, or to any intermediate position therebetween. In any case, the effective width of the pivot member can thereby be adjusted. An additional advantage in conducting any of the tests heretofore described, using the lateral extension assembly 180, is that this can be performed during the test so that the test subject can be presented with a different circumstance during each cycle of performance of the test.

A still further variation upon the ability to adjust the sensing apparatus 110, in accordance with the method of the present invention, can best be visualized upon reference to FIG. 5. The auxiliary block 140 can be mounted at any of the positions heretofore described about periphery of the platform 130 in accordance with the decisions reached by the physiotherapist in the initial evaluation. By way of illustration, if the auxiliary block is mounted in the position indicated in FIG. 5, the test subject 11 is presented with an additional circumstance to test his or her balance capability. As the test subject rocks the platform 130 in the direction of the auxiliary block 140, and beyond a horizontal attitude, the test block comes into contact with the support surface 21. However, the corresponding corner of the platform 130 adjacent to the front surface 133 of the platform is unsupported. Accordingly, the test subject will feel a tendency for the platform to rock in that direction out of the course heretofore described thereby creating an additional instability with which the test subject must deal.

As a consequence of all of the adjustments possible with the sensing apparatuses 10 and 110, the physiotherapist is armed with multiplicity of variables from which he or she can select in determining the particular test to be conducted relative to a specific test subject 11.

Additional steps in the practice of the method of the present invention include recording the times resulting from tinting of the cycles of movement of the platforms 30 and 130 along the courses heretofore described and evaluating the recorded times to determine the physical capability of the person. Thereafter, the physiotherapist plans a program of rehabilitation most closely suited to the needs of the particular test subject thereby enhancing the beneficial effects of the rehabilitation program in that it is specifically directed to the needs of the specific test subject. As previously noted, the data received for evaluation includes not only the objective data including the times recorded by the test subject, but also subjective data including the observation of the physiotherapist during the tests in noting the overall physical capability of the test subject in the performance of the tests proscribed, noting the ease and assurance with which the test subject can extend and flex those portions of the body required in the performance of the test and in maintaining the center of gravity of the test subject in the position required to perform the task involved, noting the time required for the test subject to respond to physical stimuli encountered in the performance of the task, and noting the consequence of conducting the test on the test subject such as fatigue, stress and the like.

Still further, the operation of the sensing apparatuses 10 and 110 of the present invention and in accordance with the method of the present invention, can readily be employed by the test subject as a part of the regimen of rehabilitation prescribed by the physiotherapist. Where this is done, the physiotherapist has the additional benefit of objectively noting the improvement, or lack of improvement, in the test subject by comparing the recorded times at each subsequent test with those of the original test. In addition, because of the simplicity of structure and operation of the sensing apparatuses 10 and 110, the test subject can take the sensing apparatuses home for the performance of the tests or exercises prescribed as an additional beneficial activity in the performance of the method.

Therefore, the method and apparatus for sensing and evaluating balance of the present invention are capable of use in isolating one or more of the factors influencing a person's capability of maintaining balance; can be employed as a diagnostic tool in evaluating a person's sense of balance for purposes of designing a program of rehabilitation specifically suited to that individual; can be employed by the individual in practicing the capabilities required in maintaining a sense of balance so as to develop new skills relative thereto; can be constructed in a wide variety of forms specifically directed to the particular diagnostic requirements; and are inexpensive to acquire and use and fully dependable in operation.

Although the invention has been herein shown and described in what is conceived to be the most practical and preferred embodiments, it is recognized that departures may be made therefrom within the scope of the invention which is not to be limited to the illustrative details disclosed.

Having described my invention, what I claim as new and desire to secure by Letters Patent is:

1. A method for sensing balance in a person comprising the steps of;
   positioning the person on an unstable surface of support which is a platform having a predetermined pivot point rested at a substantially fixed point; having the person move in a preinstructed manner which is to stand on said unstable surface of support and shift the person's center of gravity from side to side, or front to back and back to front, relative to said pivot point to move the platform about said pivot point: and detecting the person's ability to move in said preinstructed manner.

2. The method of claim 1 wherein said manner in which the person is preinstructed to move is to shift the person's center of gravity in cycles as nearly equal as said person is capable.

3. The method of claim 2 wherein the detecting step includes timing said cycles.

4. The method of claim 3 including the step of:
   recording the time resulting from the timing of said cycles.

5. The method of claim 4 including the step of:
   evaluating the times recorded in the recording step to determine the physical capability of said person.

6. The method of claim 2 wherein said preinstructed manner is to shift the person's center of gravity in cycles as nearly equal as said person is capable by extension and flexion of the legs.

7. The method of claim 1 wherein said platform has predetermined opposite edges, said substantially fixed point is on a substantially planar surface and said manner in which the person is preinstructed to move is to shift the person's center of gravity from side to side, or from front to back and back to front, placing in each cycle each opposite edge in turn in contact with said substantially planar surface.

8. The method of claim 7 including the step of:
   recording the time required in the cycles for said person to move the platform from one of said opposite edges in contact with said substantially planar surface to the other of said opposite edges in contact with the planar surface.

9. The method of claim 8 including the step of:
   evaluating the times recorded in the recording step to determine the physical capability of said person.

10. An apparatus for sensing balance in a person, the apparatus comprising a platform dimensioned to receive a person in supported relation thereon: a planar surface for supporting said platform for movement along a course under the impetus of a person supported on the platform in accordance with a preinstructed regimen of movement whereby the balance of the person can be sensed and wherein the platform has opposite edges individually engageable with said planar surface substantially to define the limits of said course and said platform has an upper surface dimensioned to receive said person in supported relation thereon and an opposite lower surface and said supporting means includes a pivot member mounted on said lower surface intermediate said opposite edges, and engageable with said planar surface in such a manner that said course is defined by substantially pivotal movement about the pivot member and between the points of engagement of said opposite edges of the platform with the planar surface: and means for changing the effective operable width of said pivot member and thereby changing the path of the support in said course in accordance with said preinstructed regimen of movement.

11. The apparatus of claim 10 wherein said changing means includes a second member adapted releasably to be mounted in side by side relation to the pivot member to expand the effective operable width thereof.

* * * * *

UNITED STATES PATENT AND TRADEMARK OFFICE
CERTIFICATE OF CORRECTION

PATENT NO. : 5,435,320
DATED : July 25, 1995
INVENTOR(S) : RONALD H. SEITZ

It is certified that error appears in the above-identified patent and that said Letters Patent is hereby corrected as shown below:

Column 3, line 20, delete "tile" and substitute ---the---;

line 24, delete "tile" and substitute ---the---;

line 37, delete "frown" and substitute ---from---;

Column 5, line 4, delete "tipper" and substitute ---upper---;

line 67, delete "tinting" and substitute ---timing---;

Column 7, line 35, delete "2physical" and substitute ---physical---; and

Column 10, line 37, delete "tinting" and substitute ---timing---.

Signed and Sealed this

Tenth Day of October, 1995

*Attest:*

BRUCE LEHMAN

*Attesting Officer*  Commissioner of Patents and Trademarks